United States Patent [19]

Matier

[11] Patent Number: 4,578,403
[45] Date of Patent: Mar. 25, 1986

[54] METHOD FOR TREATING GLAUCOMA BY THE TOPICAL ADMINISTRATION OF SELECTIVELY METABOLIZED BETA-BLOCKING AGENTS

[75] Inventor: William L. Matier, Libertyville, Ill.

[73] Assignee: American Hospital Supply Corporation, Evanston, Ill.

[21] Appl. No.: 619,184

[22] Filed: Jun. 11, 1984

Related U.S. Application Data

[62] Division of Ser. No. 276,658, Jun. 23, 1981, Pat. No. 4,454,154.

[51] Int. Cl.$^4$ ............... A61K 31/275; A61K 31/235; A61K 31/24
[52] U.S. Cl. .................. 514/522; 514/533; 514/534; 514/535; 514/538; 514/539; 514/540; 514/542; 514/544; 514/913
[58] Field of Search ............... 424/304, 309, 308, 311; 514/522, 533, 534, 535, 538, 539, 540, 542, 544, 913

[56] References Cited

U.S. PATENT DOCUMENTS

| | | | |
|---|---|---|---|
| 3,663,607 | 5/1972 | Barrett et al. | 424/304 |
| 3,740,444 | 6/1973 | Koppe et al. | 424/304 |
| 3,825,583 | 7/1974 | Hussain et al. | 424/311 |
| 3,839,584 | 10/1974 | Hussain et al. | 424/311 |
| 3,868,460 | 2/1975 | Koppe et al. | 424/304 |
| 3,925,446 | 12/1975 | Koppe et al. | 424/267 |
| 4,080,471 | 3/1978 | Carlsson et al. | 424/311 |
| 4,127,674 | 11/1978 | Leopold | 424/324 |
| 4,191,765 | 3/1980 | Fritsch et al. | 424/267 |
| 4,195,085 | 3/1980 | Stone | 424/248.51 |

FOREIGN PATENT DOCUMENTS

| | | |
|---|---|---|
| 0003664 | 6/1979 | European Pat. Off. |
| 41491 | 9/1981 | European Pat. Off. |
| 41492 | 9/1981 | European Pat. Off. |
| 2373513 | 8/1977 | France |

OTHER PUBLICATIONS

The Lancet, Nov. 10, 1979—p. 1028.
J. Am. M.A. 243 (11)—p. 1131.
The New Eng. J. Med., Mar. 8, 1979—p. 566.
Drug Therapy, Jul. 1979—pp. 93-94.
Ihpharma, Jun. 7, 1980—p. 7.
Ihpharma, Jul. 12, 1980—pp. 7-8.
Physicians' Desk Reference, Charles E. Baker, Jr., 34th Edition, 1232-1234 (1981).
W. P. Boger, Drugs, 18, 25-32 (1979).
L. Bonomi et al., *Glaucoma*, Eds. P. Pitts Corck and A. D. S. Caldwell, Academic Press, New York, pp. 99-105 (1980).
Demmler, *Forshr. Med.* 98 Jg (1980), No. 23, pp. 880-885.
Heel et al., *Drugs* 17 38-55 (1979).
Krieglstein et al., *Albrecht v. Graefes Arch. klin. exp. Ophthal.*, 202, 81-86 (1977).
P. Vareilles et al., Investigative Ophthalmology and Visual *Science*, vol. 16/11, 987 (1977).
T. Zimmerman, Drug Therapy, Jul. 1979, pp. 87-89.
T. J. Zimmerman and W. P. Boger, Surv. Ophthalmol.

*Primary Examiner*—Douglas W. Robinson
*Attorney, Agent, or Firm*—Bernard, Rothwell & Brown

[57] ABSTRACT

A method for the treatment of glaucoma or lowering intraocular pressure in a mammal, involving topically administering to the eye of such mammal a selectively metabolized beta-blocking compound of the formula

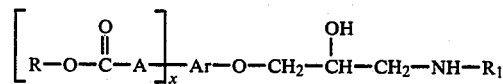

wherein R may be lower alkyl, lower alkynyl aryl, or aralkyl; A may be a direct bond, lower alkylenyl, or lower alkenyl; x may be an integer from 1 to 3; Ar may be substituted or unsubstituted aromatic; $R_1$ may be lower alkyl, lower hydroxy alkyl, lower alkenyl, lower alkynyl, or aralkyl; and pharmaceutically accepted salts thereof. Because of a relatively long duration of action of such compounds in ocular fluids and a relatively short duration of action in the systemic circulation, such compounds are useful for the treatment of excessive intraocular pressure without substantial systemic side effects.

17 Claims, No Drawings

METHOD FOR TREATING GLAUCOMA BY THE TOPICAL ADMINISTRATION OF SELECTIVELY METABOLIZED BETA-BLOCKING AGENTS

This is a division of application Ser. No. 276,658, filed June 23, 1981, now U.S. Pat. No. 4,454,154, issued June 12, 1984.

BACKGROUND OF THE INVENTION

The present invention relates to a method for the treatment of glaucoma. More particularly, the invention relates to a novel method of treatment of glaucoma or lowering of intraocular pressure by topically administering beta-adrenergic blocking agents to the eye.

Glaucoma is a condition of the eye characterized by increased intraocular pressure. Untreated, the condition can eventually lead to irreversible retinal damage and blindness. Conventional therapy for glaucoma has involved topical administration of pilocarpine and/or epinephrine, administered to the eye several times daily.

Various beta-blocking agents may also be used to lower intraocular pressure. Such use is described, for example, in reviews by W. P. Boger in Drugs, 18, 25–32 (1979) and by T. J. Zimmerman & W. P. Boger in Surv. Ophthalaol., 23(c), 347 (1979). The use of beta-blockers for the treatment of glaucoma is also described in the patent literature. For example, U.S. Pat. No. 4,195,085 to Stone discloses a method for treatment of glaucoma by the ocular administration of a beta-blocking compound, timolol maleate. U.S. Pat. No. 4,127,674 discloses treating glaucoma with labetalol, a known antagonist of both alpha and beta adrenergic receptors. However, these methods also possess significant drawbacks, in that the absorption of the beta-blocking compound into the systemic circulation can cause undesirable side effects. Such side effects result from prolonged beta-blocking action on the heart, bronchioles and blood vessels. For example, according to *Physicians' Desk Reference*, Charles E. Baker, Jr., 35th Edition, 1981, p. 1233, adverse reactions to the topical use of timolol maleate can include bronchospasm, heart failure, as well as cardiac conduction defects. Accordingly, there is a need for a method of treatment for glaucoma or for lowering intraocular pressure utilizing beta-blocking agents which are relatively free of unwanted systemic side-effects.

Certain beta-blocking agents which contain enzymatically labile ester groups are known to exhibit short-acting beta-blocking effects in the systemic circulation. Such short-acting beta-blocking compounds (SABBs) have been suggested for treatment or prophylaxis of cardiac disorders as a means for reducing heart work or improving rhythmicity for a short duration. Such short-acting beta-blocking compounds avoid the sometimes counterproductive effects of conventional beta-blocking agents, whose effects are typically long-lived and, therefore, difficult to precisely control.

SUMMARY OF THE INVENTION

In accordance with the present invention, disclosed herein is a method for the treatment of glaucoma or for lowering intraocular pressure in a mammal, comprising topically administering to the eye of such mammal a beta-blocking compound of the formula:

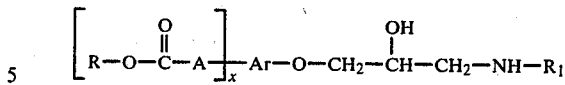

wherein R is lower alkyl, lower cycloalkyl, lower alkenyl, lower alkynyl lower alkyl or aryl carboxymethyl, lower haloalkyl, aralkyl or aryl; A is a direct bond, lower alkylenyl, or lower alkenyl; x is an integer from 1 to 3, provided that when x is greater than 1, different occurrences of the

group may be the same or different; Ar is unsubstituted aromatic or aromatic substituted with lower alkyl, lower alkenyl, lower alkynyl, lower alkoxy, halogen, acetamido, amino, nitro, lower alkylamino, hydroxy, lower hydroxyalkyl or cyano; $R_1$ is lower alkyl, lower hydroxyalkyl, lower alkenyl, lower alkynyl or aralkyl; or a pharmaceutically acceptable salt thereof.

DETAILED DESCRIPTION OF THE INVENTION

The above-mentioned short-acting beta-blocking compounds effectively reduce intraocular pressure in the eyes of mammals when topically administered. Because of their short-lived duration of action in the systemic circulation, side-effects produced by their migration out of the eye are consequently reduced. It has further been discovered that certain of these compounds show an increased longevity of effect when present in the ocular fluid, compared to the duration of their systemic effects. Consequently, the present invention resides in the treatment of glaucoma or lowering intraocular pressure with a beta-blocking compound which exhibits relatively long duration of action while in the ocular fluid, but which is subject to relatively rapid breakdown into inactive metabolites upon passage to the systemic circulation.

Compounds administered by the method of the present invention are represented by the formula:

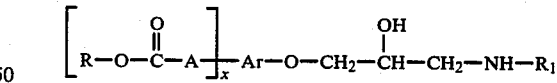

wherein R represents lower alkyl of straight or branched carbon chains from 1 to about 10 carbon atoms, lower cycloalkyl of from 3 to about 5 carbon atoms, lower alkenyl of from 2 to about 5 carbon atoms, lower alkynyl of from 2 to about 5 carbon atoms, lower alkyl carboxymethyl in which the alkyl portion contains from 1 to about 5 carbon atoms, aryl carboxymethyl in which the aryl portion contains from 6 to about 8 carbon atoms, aryl of from 6 to about 10 carbon atoms or aralkyl wherein the alkyl portion contains from about 1 to about 5 carbon atoms and the aryl portion represents substituted or unsubstituted monocyclic or polycyclic aromatic or heterocyclic ring systems of from 6 to about 10 carbon atoms; A represents a direct bond between the ester group and Ar, lower alkylenyl of from 1 to about 10 carbon atoms, or alkenyl of from 2 to about 10 carbon atoms; x represents an integer from 1 to 3, provided that when x is greater than 1, different occurrences of the

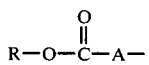

group may be the same or different; Ar represents substituted or unsubstituted aromatic, including monocyclic, polycyclic and heterocyclic ring systems, wherein aromatic substituents include lower alkyl of from 1 to about 10 carbon atoms, lower alkenyl of from 2 to about 10 carbon atoms, lower alkynyl of from 2 to about 10 carbon atoms, lower alkoxy of from 1 to about 10 carbon atoms, halogen, acetamido, amino, nitro, lower alkylamino, of from 1 to about 10 carbon atoms, hydroxy, lower hydroxyalkyl of from 1 to about 10 carbon atoms, and cyano; $R_1$ represents lower alkyl of from 1 to about 10 carbon atoms, such as methyl, propyl, hexyl, isopropyl, and the like; lower hydroxyalkyl of from 2 to about 10 carbon atoms, such as hydroxyethyl, hydroxy-t-butyl, hydroxyisopropyl and the like; lower alkenyl of from 3 to about 10 carbon atoms, such as allyl; lower alkynyl of from 3 to about 10 carbon atoms such as dimethylpropargyl and the like; or aralkyl wherein the alkyl portion contains from 1 to about 5 carbon atoms and the aryl portion contains from 6 to about 10 carbon atoms, such as benzyl, phenethyl, naphthylethyl, 3,4-dimethoxyphenethyl and the like. Such compounds may be administered as their pharmaceutically acceptable acid addition salts, e.g., as the hydrochloride, sulfate, phosphate, gluconate, tartrate, et cetera.

In preferred compounds, A is a direct bond, lower alkylenyl of from 3 to about 5 carbon atoms, such as methylene, ethylene, butylene and the like, or lower alkenyl of from 2 to about 5 carbon atoms, such as ethenyl, 2-propenyl, 2-butenyl, and the like and x is 1 or 2, and in particularly preferred compounds, Ar is phenyl, x is 1 or 2 and A is a direct bond, lower alkylenyl of from 1 to 3 carbon atoms, or lower alkenyl of 2 carbon atoms. It has been found that the compounds in which Ar is phenyl and para-substituted, beta-blocking potency and shortness of duration of action in blood are improved when A is lower alkylene with 1 or more carbons, i.e., the ester group is isolated from the aromatic ring by at least one methylene unit. Alternatively, in compounds in which Ar is phenyl, at least one of the ester-containing groups,

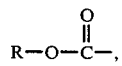

is advantageously in the ortho-position with respect to the side chain. It is surprising and presently unexplained, that two configurations of the compounds of the present invention, para-substitution with an ester carbonyl isolated from the aromatic ring and ortho-substitution with the ester carbonyl attached directly to the aromatic ring, provide enhanced beta-blocking potency and relatively short duration of action in blood.

The ester substituent, R, in preferred compounds, is lower alkyl of from 1 to about 5 carbon atoms, such as methyl, ethyl, n-butyl, n-pentyl, and the like; lower alkenyl of from 2 to about 5 carbon atoms, such as ethenyl, 2-propenyl, 2-methyl-3-butenyl and the like; lower alkynyl of from 3 to about 5 carbon atoms, such as propargyl, methylpropargyl and the like, or lower cycloalkyl of from 3 to about 5 carbon atoms such as cyclopropyl, cyclopentyl, 2-methylcyclopropyl, and the like; $R_1$ is preferably lower alkyl of from 1 to about 5 carbon atoms such as methyl, ethyl, propyl, t-butyl, pentyl and the like, lower hydroxyalkyl of from 1 to about 5 carbon atoms, such as hydroxyethyl, hydroxy-t-butyl, hydroxyisopropyl and the like; lower alkynyl of from 3 to about 5 carbon atoms such as propargyl, dimethylpropargyl and the like; or aralkyl, wherein the alkyl portion contains from 1 to about 5 carbon atoms and the aryl portion contains from 6 to about 10 carbon atoms, such as benzyl, phenethyl, dimethoxyphenethyl, naphthylethyl, phenylbutyl, and the like.

Preferred aromatic substituents include lower alkyl of from 1 to about 5 carbon atoms, lower alkenyl of from 2 to about 5 carbon atoms, lower alkoxy of from 1 to about 5 carbon atoms, halogen, acetamido, amino, nitro, lower alkylamino of from 1 to about 5 carbon atoms, hydroxy, lower hydroxyalkyl of from 1 to about 5 carbon atoms, and cyano. Particularly preferred aromatic substituents are lower alkyl of from 1 to about 5 carbon atoms, fluoro, chloro, cyano, and alkoxy.

The compounds described herein, as well as their methods of preparation, are disclosed in co-pending U.S. patent application, Ser. No. 211,345, which is hereby incorporated by reference. In addition, certain of the compounds which may be employed in the method of the present invention are known in the art. For instance, compounds of the above formula in which A is ethenyl are described in U.S. Pat. No. 4,191,765 and in Japanese unexamined patent application (Kokai) No. 7400247 (see also *Chemical Abstracts*, 80, 95546W (1974)). Compounds of the above formula in which $R_1$ is 1,1-dimethyl-2-hydroxyethyl are described in British Pat. No. 1,364,280, and compounds in which $R_1$ is dimethylpropargyl are described in British Pat. No. 1,450,287.

The compounds of this invention are advantageously administered topically to the eye in the form of a solution, ointment, or solid insert such as is described in U.S. Pat. No. 4,195,085 to allow controlled or delayed release of the drug. Formulations may contain the active compound, preferably, in the form of a soluble acid addition salt, in amounts ranging from about 0.01 to about 10% by wt., preferably, from about 0.5% to about 5% by wt. Unit dosages of the active compound can range from about 0.001 to about 5.0 mg., preferably from about 0.05 to about 2.0 mg. The dosage administered to a patient will depend upon the patient's needs and the particular compounds employed.

Carriers used in the preparations of the present invention are preferably non-toxic pharmaceutical organic or inorganic compositions such as water; mixtures of water and water-miscible solvents, such as lower alcohols; mineral oils; petroleum jellies; ethyl cellulose; polyvinylpyrrolidone and other conventional carriers. In addition, the pharmaceutical preparations may also contain additional components such as emulsifying, preserving, wetting and sterilizing agents. These include polyethylene glycols 200, 300, 400 and 600, carbowaxes 1,000, 1,500, 4000, 6,000 and 10,000, bacteriocidal components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

The method of treatment of this invention advantageously involves the topical administration of eye drops containing the active compound. Formulations for eye drops preferably include the active compound as a soluble acid addition salt in a properly buffered, sterile, aqueous isotonic solution.

The compounds employed in the method of the present invention are ester group-containing beta-blockers that have a selective, localized, beta-blocking effect in the dye after topical administration. Such compounds are thought to be rapidly metabolized by plasma and/or liver esterases into inactive by-products, upon entering the systemic circulation. It has been discovered that these same compounds are relatively stable in ocular fluids, i.e., lacrimal fluids and aqueous humor. Consequently, such compounds are useful for the treatment of glaucoma or for lowering intraocular pressure since they remain stable when topically applied to the eye but rapidly metabolize when subsequently absorbed into the systemic circulation.

Some of the compounds break down in the aqueous humor more rapidly than others. Such compounds may advantageously be employed when only a temporary reduction in intraocular pressure is desired, say for diagnostic procedures. Longer-acting compounds are generally used for effecting longer-term reductions in intraocular pressure, such as is desired when treating chronic glaucoma. Thus, the method of the present invention provides a very useful therapeutic alternative for the treatment of glaucoma or for lowering intraocular pressure.

The in vitro studies hereinafter described indicate that the compounds used in the method of the present invention will undergo different rates of enzymatic hydrolysis depending on their location within the body (see Table I). For example, the compound of Example I is completely hydrolyzed within 60 minutes in liver homogenate while only 0.3% hydrolyzed after one hour in aqueous humor, and only 1.3% hydrolyzed after two hours. The compound of Example V is less stable in aqueous humor, hydrolyzing 3.6% after one hour, 13.4% after two hours.

The present invention is further illustrated by the following examples which are not intended to be limiting.

EXAMPLES I-V

The enzymatic hydrolysis rates of the following compounds were examined in dog blood, liver homogenate, and aqueous humor:

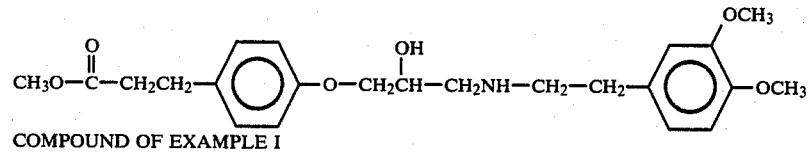
COMPOUND OF EXAMPLE I

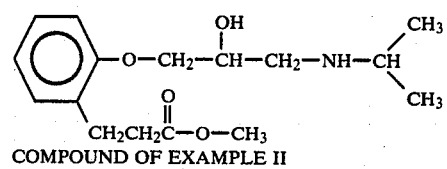
COMPOUND OF EXAMPLE II

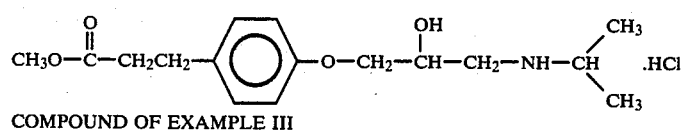
COMPOUND OF EXAMPLE III

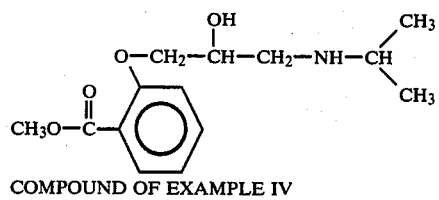
COMPOUND OF EXAMPLE IV

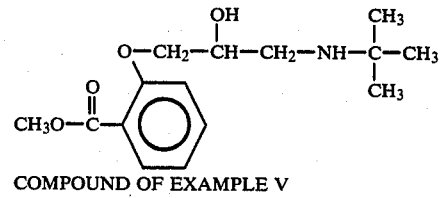
COMPOUND OF EXAMPLE V

All of the compounds tested were synthesized in accordance with the examples of U.S. patent application Ser. No. 211,345. Acetonitrile was "HPLC" grade. Distilled water was used to dissolve the compounds and 0.01N HCl was used to dissolve compounds requiring an acidic pH for dissolution.

Fresh aqueous humor was collected from eyes of dogs using a 23 gauge needle while fresh dog blood was collected into heparinized Vacutainer ® tubes. Fresh liver was homogenized in 0.9% NaCl using a Potter-Elvehjem Teflon pestle and glass homogenizer making a 25% (W/V) homogenate.

A 0.5 ml aliquot of dog aqueous humor, blood, or liver homogenate was incubated with 12.5 μg (0.5 ml) of beta-blocker in a Dubnoff shaking metabolic incubator at 37° C. for 60 and 120 minutes. Denatured tissue controls were prepared by adding 2.0 ml of acetonitrile into 0.5 ml of aqueous humor, blood, or liver homogenate to destroy esterase activities prior to addition of the beta-blockers. These controls were then incubated at 37° C. for 120 minutes. After 60 and 120 minutes, the incubations were terminated by addition of 2 ml of acetonitrile and immediately mixed using a Vortex ® mixer to stop esterase activities.

All samples were centrifuged at 4000 RPM for 10 minutes to sediment denatured proteins. The resultant supernatants were transferred to WISP ® vials and analyzed by high pressure liquid chromatography. The hydrolysis of beta-blockers in aqueous humor, blood, and liver homogenate was determined by disappearance of the compounds. The extent of enzymatic hydrolysis in each tissue was determined by comparing the amount of each compound (absolute peak area) recovered at each time point to the amount of each compound (absolute peak area) in denatured tissue control and aqueous control samples.

All of the compounds examined were initially tested for chemical hydrolysis in 0.1N potassium phosphate buffer, pH 7.40, and all were found to be stable for at least three hours (data not shown).

Table 1 summarizes the results of these experiments. The extent of hydrolysis is expressed in terms of the amount of each compound recovered after the incubation period relative to the amount of each compound recovered in the denatured tissue control. Most of the SABBs were readily hydrolyzed very rapidly (55.5–98.8% in 120 minutes) when incubated with dog blood and liver homogenate. In contrast, all of the compounds tested were resistant to enzymatic hydrolysis by esterases in dog aqueous humor having hydrolysis rates of 0.3–3.6% in 60 minutes and 1.3–13.4% in 120 minutes.

EXAMPLE VI

The intraocular pressure lowering effect of the compounds of this invention are demonstrated in rabbits with normotensive eyes.

Sterile, isotonic saline solutions of each of the compounds used in procedures of Examples I, II, III, IV, and V are prepared by dissolving 10, 30 and 100 mg. samples of each of the active compounds in 1 ml. of saline to give 1%, 3% and 10% solutions with pH about 6.0–7.0. Free amines require one equivalent of HCl to effect dissolution.

The intraocular pressure lowering effect of each compound is determined by treating the eyes of healthy rabbits with the above solutions. Three rabbits are used to evaluate the effect of each drug concentration. A standard dose of 50 μl. of each drug solution is applied to one eye of each of the three rabbits. Intraocular pressure of both eyes is measured with a pressure tonograph or a Mackay-Marg Tonometer before drug administration and at 15, 30, 45, 60, 120, 180, 240, 300, 360, 420 and 480 min. after dosing. Control rabbits are treated similarly with sterile isotonic saline solution. Intraocular pressure lowering in the treated dyes is compared with the untreated eyes, with saline treated eyes and with predrug pressures. All of the test compounds show intraocular pressure-lowering activity.

EXAMPLE VII

The experiment of Example VI is repeated in all essential details, except that the following compounds are tested:

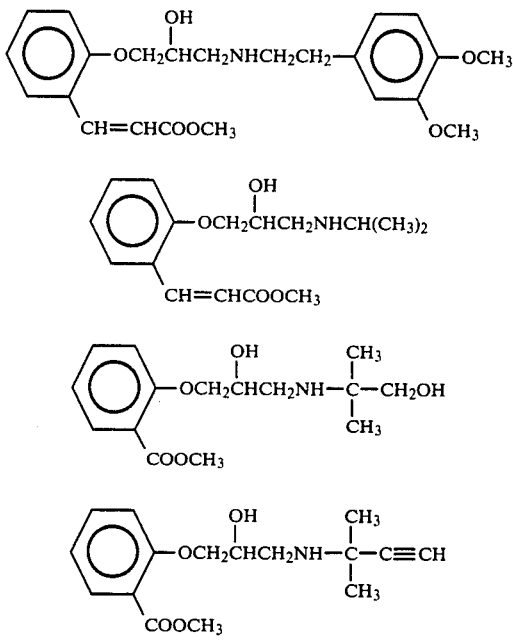

Each of the test compounds exhibit intraocular pressure-lowering activity.

EXAMPLE VIII

The experiment of Example VI is repeated in all essential details, except that rabbits which have corticosteroid induced ocular hypertension, as described by Bonomi, L., et al., Glaucoma, Eds. R. Pittscrick, A. D. S. Caldwell, Academic Press, New York, pp. 98–107 (1980), are substituted for the normotensive rabbits. Each of the test compounds exhibit intraocular pressure-lowering activity in this model.

TABLE 1

ENZYMATIC HYDROLYSIS OF SABBs BY DOG BLOOD, LIVER HOMOGENATE, AND AQUEOUS HUMOR

| COMPOUND OF EXAMPLE | % HYDROLYZED[1] | | | | | |
|---|---|---|---|---|---|---|
| | BLOOD | | LIVER | | AQUEOUS HUMOR | |
| | 60 min | 120 min | 60 min | 120 min | 60 min | 120 min |
| I | 76.6 | 94.9 | 100 | 100 | 0.3 | 1.3 |
| II | 32.0 | 55.5 | 100 | 100 | 1.5 | 7.3 |
| III | 69.0 | 89.4 | 100 | 100 | 2.4 | 7.5 |
| IV | 65.7 | 88.5 | 11.9 | 40.0 | 3.6 | 8.2 |
| V | 85.6 | 98.8 | 100 | 100 | 3.6 | 13.4 |

[1]Data at each time point are expressed relative to denatured tissue control.

What is claimed is:

1. A method for treating glaucoma or for lowering intraocular pressure in a mammal, which comprises topically applying to the eye of such mammal an intraocular pressure-lowering effective amount of a compound represented by the formula:

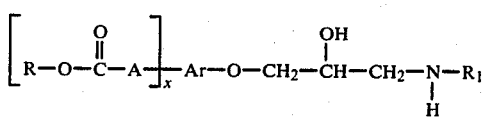

wherein R represents lower alkyl of straight or branched carbon chains from 1 to about 10 carbon atoms, lower cycloalkyl of from 3 to about 5 carbon atoms, lower alkenyl of from 2 to about 5 carbon atoms, lower alkynyl of from 2 to about 5 carbon atoms, lower alkyl carboxymethyl in which the alkyl portion contains from 1 to about 5 carbon atoms, aryl carboxymethyl in which the aryl portion contains from 6 to about 8 carbon atoms, aryl of from 6 to about 10 carbon atoms or aralkyl wherein the alkyl portion contains from about 1 to about 5 carbon atoms and the aryl portion represents substituted or unsubstituted monocyclic or polycyclic aromatic of from 6 to about 10 carbon atoms; A is a direct bond, lower alkylene or lower alkenylene; x is an integer from 1 to 3, provided that when x is greater than 1, different occurrences of the

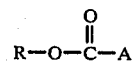

group may be the same or different; Ar is phenyl or napthyl substituted with acetamido, amino, nitro, lower alkylamino, hydroxy, lower hydroxyalkyl, or cyano; $R_1$ is lower alkyl, lower hydroxyalkyl, lower alkenyl, lower alkynyl, or aralkyl; or a pharmaceutically acceptable salt thereof.

2. The method of claim 1 wherein A is a direct bond, an alkylene group of from 1 to 5 carbon atoms or alkenylene of from 2 to about 5 carbon atoms, and x is 1 or 2.

3. The method of claim 1 wherein Ar is phenyl substituted with acetamido, amino, nitro, lower alkylamino, hydroxy, lower hydroxyalkyl, or cyano; x is 1 or 2, A is a direct bond, an alkylene group of from 1 to about 3 carbon atoms, or alkenylene of from 2 to about 3 carbon atoms and at least one of the

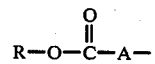

groups is in the ortho position with respect to the

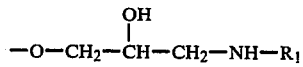

group.

4. The method of claim 1 wherein Ar is phenyl substituted with acetamido, amino, nitro, lower alkylamino, hydroxy, lower hydroxyalkyl, or cyano; x is 1 or 2; A is alkylene of from 1 to about 3 carbon atoms, or alkenylene of from 2 to about 3 carbon atoms and at least one of the

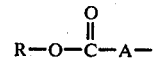

groups is in the para position with respect to the

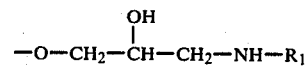

group.

5. The method of claim 3 wherein R is lower alkyl of from 1 to about 5 carbon atoms.

6. The method of claim 4 wherein R is lower alkyl of from 1 to about 5 carbon atoms.

7. The method of claim 1 wherein the compound is of the formula

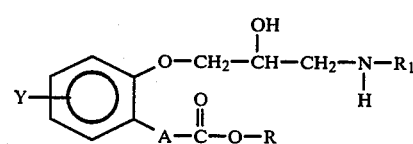

wherein A is an alkylene group of from 1 to about 3 carbon atoms, or alkenyl of from 3 to about 5 carbon atoms; R is lower alkyl of from 1 to about 5 carbon atoms, lower alkenyl of from 2 to about 5 carbon atoms, or lower alkynyl of from 3 to about 5 carbon atoms; Y is acetamido, amino, nitro, lower alkylamino of from 1 to about 5 carbon atoms, hydroxy, lower hydroxyalkyl of from 1 to about 5 carbon atoms or cyano; and $R_1$ is lower alkyl of from 1 to about 5 carbon atoms, lower hydroxyalkyl of from 2 to about 5 carbon atoms, lower alkenyl of from 3 to about 5 carbon atoms, or aralkyl wherein the alkyl portion contains from 1 to about 5 carbon atoms and the aryl portion contains from 6 to about 10 carbon atoms.

8. The method of claim 1 wherein the compound of the formula:

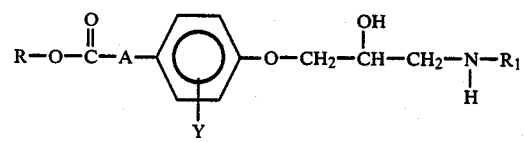

wherein A is alkylene of from 1 to about 3 carbon atoms, R is lower alkyl of from 1 to about 5 carbon atoms, lower alkenyl of from 2 to about 5 carbon atoms or lower alkynyl of from 3 to about 5 carbon atoms; Y is acetamido, amino, nitro, lower alkylamino of from 1 to about 5 carbon atoms, hydroxy, lower hydroxyalkyl of from 1 to about 5 carbon atoms or cyano; and $R_1$ is lower alkyl of from 1 to about 5 carbon atoms, lower hydroxyalkyl of from 2 to about 5 carbon atoms, lower alkynyl of from 3 to about 5 carbon atoms, or aralkyl wherein the alkyl portion contains from 1 to about 5 carbon atoms and the aryl portion contains from 6 to about 10 carbon atoms.

9. The method of claim 1 wherein the applied compound is

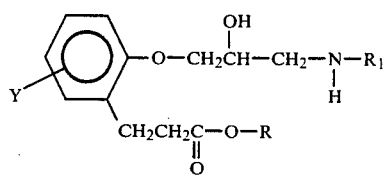

wherein R is methyl, ethyl or propargyl, Y is acetamido, amino, nitro, lower alkylamino of from 1 to about 5 carbon atoms, hydroxy, lower hydroxyalkyl of from 1 to about 5 carbon atoms or cyano; and $R_1$ is isopropyl, t-butyl, hydroxy-t-butyl, dimethylpropargyl, or 3,4-dimethoxyphenethyl.

10. The method of claim 1 wherein the applied compound is

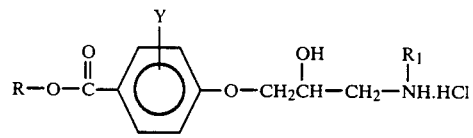

wherein R is methyl, ethyl or propargyl, Y is acetamido, amino, nitro, lower alkylamino of from 1 to about 5 carbon atoms, hydroxy, lower hydroxyalkyl of from 1 to about 5 carbon atoms or cyano; and $R_1$ is isopropyl, t-butyl, hydroxy-t-butyl, dimethylpropargyl, or 3,4-dimethoxyphenethyl.

11. The method of claim 1 wherein the applied compound is

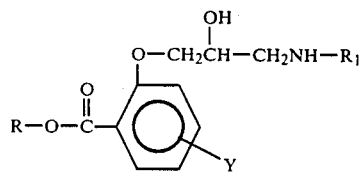

wherein R is methyl, ethyl, or propargyl, Y is acetamido, amino, nitro, lower alkylamino of from 1 to about 5 carbon atoms, hydroxy, lower hydroxyalkyl of from 1 to about 5 carbon atoms or cyano; and $R_1$ is isopropyl, t-butyl, hydroxy-t-butyl, dimethylpropargyl, or 3,4-dimethoxyphenethyl.

12. The method of claim 1 wherein the applied compound is

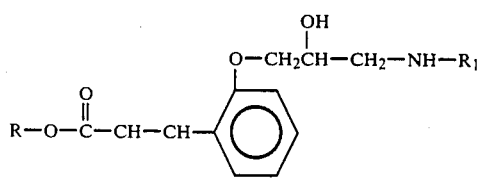

wherein R is methyl, ethyl, or propargyl, Y is acetamido, amino, nitro, lower alkylamino of from 1 to about 5 carbon atoms, hydroxy, lower hydroxyalkyl of from 1 to about 5 carbon atoms or cyano; and $R_1$ is isopropyl, t-butyl, hydroxy-t-butyl, dimethylpropargyl, or 3,4-dimethoxyphenethyl.

13. The method of claim 1 wherein the compound is administered as a solution of about 0.01% to about 10% by weight of the active ingredient in an ophthalmologically acceptable carrier.

14. The method of claim 1 wherein the compound is administered as a solution of about 0.5% to about 5% by weight of the active ingredient in an ophthalmologically acceptable carrier.

15. The method of claim 1 wherein the unit dosage of the active compound ranges from about 0.001 mg to about 5.0 mg.

16. The method of claim 1 wherein the unit dosage of the active compound ranges from about 0.05 mg to about 2.0 mg.

17. The method of claim 1 wherein the active compound is contained in a sterile, aqueous, buffered, isotonic solution.

* * * * *